(12) United States Patent
Belliard

(10) Patent No.: US 8,465,495 B2
(45) Date of Patent: Jun. 18, 2013

(54) SURGICAL TOOL FOR TENSIONING A FLEXIBLE MEMBER

(75) Inventor: Karl P. Belliard, La Membrolle sur Longuenee (FR)

(73) Assignee: Zimmer Spine, Bordeaux (FR)

( * ) Notice: Subject to any disclaimer, the term of this patent is extended or adjusted under 35 U.S.C. 154(b) by 538 days.

(21) Appl. No.: 12/613,101

(22) Filed: Nov. 5, 2009

(65) Prior Publication Data

US 2010/0121387 A1    May 13, 2010

(30) Foreign Application Priority Data

Nov. 7, 2008  (EP) .................................... 08305790

(51) Int. Cl.
*A61B 17/58* (2006.01)
*A61B 17/60* (2006.01)

(52) U.S. Cl.
USPC .......................................... 606/103; 606/263

(58) Field of Classification Search
USPC .................. 606/86 A, 86 R, 103, 246–279
See application file for complete search history.

(56) References Cited

U.S. PATENT DOCUMENTS

| | | | |
|---|---|---|---|
| 5,355,913 A | 10/1994 | Green et al. | |
| 5,449,361 A | 9/1995 | Preissman | |
| 5,476,465 A | 12/1995 | Preissman | |
| 5,540,698 A | 7/1996 | Preissman | |
| 5,665,088 A | 9/1997 | Gil et al. | |
| 5,769,898 A | 6/1998 | Jisander | |
| 5,935,133 A | 8/1999 | Wagner et al. | |
| 5,964,769 A | 10/1999 | Wagner et al. | |
| 6,053,921 A | 4/2000 | Wagner et al. | |
| 6,099,527 A | 8/2000 | Hochschuler et al. | |
| 6,391,030 B1 | 5/2002 | Wagner et al. | |
| 6,682,533 B1 | 1/2004 | Dinsdale et al. | |
| 6,695,852 B2* | 2/2004 | Gleason | 606/103 |
| 6,761,722 B2* | 7/2004 | Cole et al. | 606/74 |
| 7,207,357 B2 | 4/2007 | de Oliveira | |
| 7,326,222 B2* | 2/2008 | Dreyfuss et al. | 606/144 |
| 2009/0054933 A1* | 2/2009 | Mickiewicz et al. | 606/86 A |
| 2009/0138048 A1 | 5/2009 | Baccelli et al. | |
| 2009/0182379 A1 | 7/2009 | Baccelli et al. | |

FOREIGN PATENT DOCUMENTS

| | | |
|---|---|---|
| DE | 868045 C | 2/1953 |
| EP | 0019062 A | 11/1980 |
| EP | 0597257 A | 5/1994 |
| EP | 0780096 A | 6/1997 |
| EP | 1731109 A | 12/2006 |
| EP | 1933743 | 6/2008 |
| WO | 2007034112 A | 3/2007 |

\* cited by examiner

*Primary Examiner* — Eduardo C Robert
*Assistant Examiner* — Michelle C Eckman
(74) *Attorney, Agent, or Firm* — Seager, Tufte & Wickhem, LLC

(57) ABSTRACT

A surgical tool for tensioning a flexible member of a vertebral device, the flexible member having at least one end portion to which tension is applied. The surgical tool includes a longitudinal member having a longitudinal axis, a first end provided with an element for securing in rotation at least one end portion of the flexible member with the first end of the longitudinal member, and a second end provided with a handling element. The surgical tool also includes a guiding structure comprising a first end adapted to be applied against the body of the vertebral device, and at least one guiding element for guiding in rotation the longitudinal member about the longitudinal axis. The guiding structure maintains the longitudinal axis of the longitudinal member with respect to the body, whereby the rotation of the longitudinal member with the handling element produces the tensioning of the flexible member.

11 Claims, 4 Drawing Sheets

SURGICAL TOOL FOR TENSIONING A FLEXIBLE MEMBER

RELATED APPLICATION

This application claims priority to European Patent Application No. 08 305 790.1 filed Nov. 7, 2008, incorporated herein by reference.

TECHNICAL FIELD

The embodiments described herein relate to a surgical tool for tensioning a flexible member used for fastening a vertebral device on a bony element, or bony elements, by forming at least one loop around the bony element(s).

BACKGROUND

The spine is made up of a superposition of vertebrae, that are normally aligned along a vertebral axis, going from the lumbar vertebrae to the cervical vertebrae, with each vertebra presenting a posterior wall from which there projects a spinous process and two side edges having walls from which there project the ribs and/or transverse processes. When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve.

In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices are used that have screws for insertion into the vertebrae or hooks for inserting along the inside wall of the spinal canal, associated with rods for interconnecting the screws or the hooks.

The hooks are generally inserted in pairs in each vertebra and on either side close to the pedicles, the heads of the hooks projecting from the posterior wall of a vertebra, one on either side of the spinous process. The heads may be tulip-shaped, for example, and they are suitable for receiving a rod which is secured by means of a nut screwed onto the head and bearing against the rod. Rows constituted by the heads of the hooks situated on either side of the spinous processes are interconnected and held in fixed position by two rods that are parallel to each other and to the axis of the spine.

Nevertheless, using such hooks may be difficult, since the operator is attempting to avoid harming the spinal cord that extends in the center of the spinal canal, since that could lead to paralysis for the patient.

The use of screws makes it possible to reduce the risks of such surgery. They likewise have tulip-shaped heads and they are inserted in pairs in the posterior walls of vertebrae in the pedicles on either side of the spinous processes. Thus, the screws constitute fastening points in the vertebrae for holding them relative to one another. Nevertheless, the screws are necessarily inserted into the pedicles of the vertebrae, and under certain circumstances, the pedicles may be small in size or they may be damaged.

A problem which arises is how to obtain such fastening points when it is not possible to introduce screws into the vertebrae in the curved portion, and when using hooks would be too dangerous. Flexible band systems for fastening to a vertebra can be used to solve this problem. For instance, the system shown as an example in accompanying FIG. 1 is one solution.

It comprises a connection piece 12 constituted by two jaws 20 and 22 that are coupled together at one end about an axis 24. The two jaws have recesses 25 enabling a rod 18 to be put into place and allowing a flexible member such as a band or cord to pass through, the flexible member 14 forming a loop 28 on one side of the connection piece 12 and two ends 30 and 32, which may be free ends of the flexible member, on the other side of said piece. The connection system also has a locking member 16 constituted by a screw that can be engaged in the ends of the jaws 20 and 22 remote from their hinged ends. The portions of the flexible member 14 that are engaged in the recesses are secured to the connection piece by being pinched between the walls of the recesses in the connection piece and the rod 18 when the locking member 16 is fully engaged.

It can be understood that in order to ensure that said assembly is properly fastened on a transverse process, on a rib, or on a portion of the posterior portion of a vertebra, it is necessary to exert tension on the ends 30 and 32 of the flexible member 14.

In the case of an intervertebral implant which is inserted between the spinal processes of two adjacent vertebrae, it is also necessary to secure the body of the implant to the spinal processes.

The securing of the implant body to the spinal processes is generally obtained by means of a flexible member such as flexible member 14, the two extremities of which are secured to the implant body.

Accompanying FIG. 2 illustrates such an intervertebral implant. The implant 50 comprises a body 52 provided with two opposite openings 54 to 56 to receive the spinal processes of the vertebrae. The implant further comprises a flexible member 58 forming two loops 58a and 58b adapted to pass around the spinal processes of the two vertebrae. The flexible member is secured to the implant body 52 by means of a securing device which includes a movable member 62 which can be moved with respect to the body itself by means of a control screw 64. Two portions of the flexible member are pinched between the body 52 and the movable member 62. The free extremities 58c and 58d of the flexible member extend out of the implant body 62.

Before securing the flexible member 58 to the implant, it is necessary to apply suitable tension to the extremities of the flexible member to obtain proper securing of the implant with the vertebrae.

In some cases, one extremity of the flexible member is directly secured to the body of the intervertebral implant, and tension is to be applied only to one free end of the flexible member.

In the present description, the wording "vertebral device" means any mechanical device used in connection with the treatment of the spine which is secured to a vertebra or to a rib by means of a flexible member including, for example, fastening devices and intervertebral implants.

The PCT application WO 2007/034112 describes a surgical tool for tensioning a flexible member which is used to secure a vertebral device, namely a fastening device, to a bone element and especially a vertebra or a rib.

This surgical tool is well adapted to different surgical operations but in some particular cases it is not suitable because it requires significant free space and the portion of the flexible member which cooperates with the tool is in the shape of a loop.

SUMMARY

An object of the present invention is to provide a surgical tool for tensioning a flexible member in such a manner that the tension is applied to at least one free extremity of the flexible member.

To achieve this goal, one embodiment provides a surgical tool for tensioning a flexible member of a vertebral device having a body, said flexible member having at least one end portion to which tension should be applied, comprising:
- a longitudinal member having a longitudinal axis, a first end provided with an element for securing in rotation at least one end portion of said flexible member with said first end of the longitudinal member, and a second end provided with a handling element; and
- a guiding structure comprising a first end adapted to be applied against said body of the vertebral device, and at least one guiding element for guiding in rotation said longitudinal member about said longitudinal axis, said guiding structure maintaining the longitudinal axis of the longitudinal member with respect to said body, whereby the rotation of said longitudinal member with the handling element produces the tensioning of said flexible member.

According to one embodiment, the rotation of the longitudinal member produces the rolling of said at least one end portion of said flexible member about said first end of the longitudinal member.

According to one embodiment, the surgical tool comprises an element for securing the extremities of the flexible member comprising a slot designed for receiving said at least one extremity of the flexible member.

According to one embodiment, the surgical tool comprises a longitudinal member being a rod having first and second ends, and the guiding structure is a tubular member having first and second ends and adapted to receive said rod in rotation. The second end of the tubular member may be provided with a second handling element.

According to an embodiment, the surgical tool further comprises a locking controllable member for securing in rotation said longitudinal member and said guiding member. In this case, when the surgeon has applied correct tension to the flexible member, the surgeon can easily interlock the two parts of the surgical tool to maintain the tension.

According to another embodiment, the surgical tool further comprises a screwing tool for cooperating with a screw of the intervertebral device.

BRIEF DESCRIPTION OF THE DRAWINGS

Other characteristics and advantages of the invention will appear clearer on reading the following detailed description of embodiments of the invention given by way of non-limiting examples. This detailed description refers to the accompanying figures in which.

DETAILED DESCRIPTION

Figure 3:
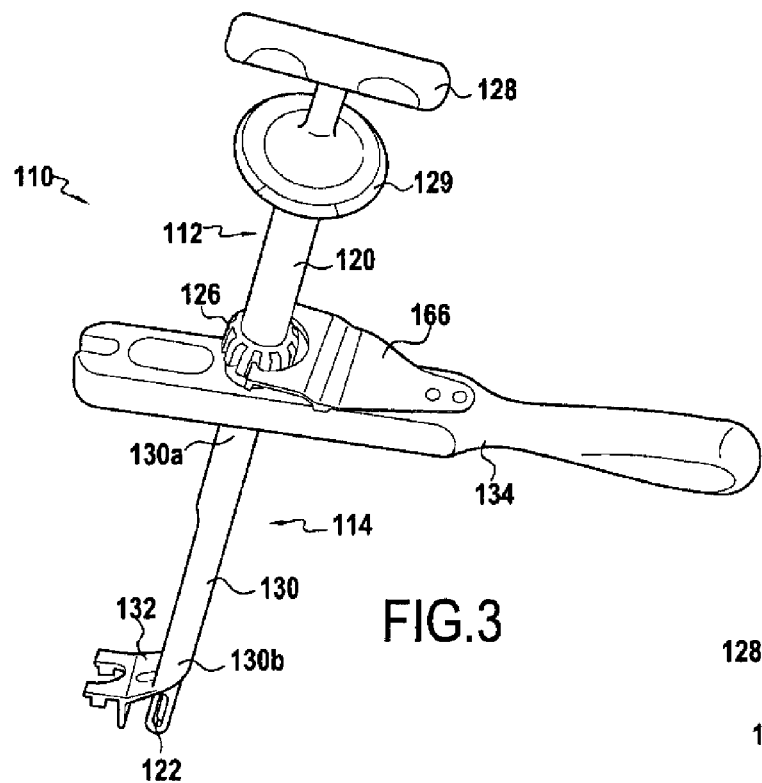
FIG. 3 is a perspective view of an embodiment of the surgical tool.
Figure 4:
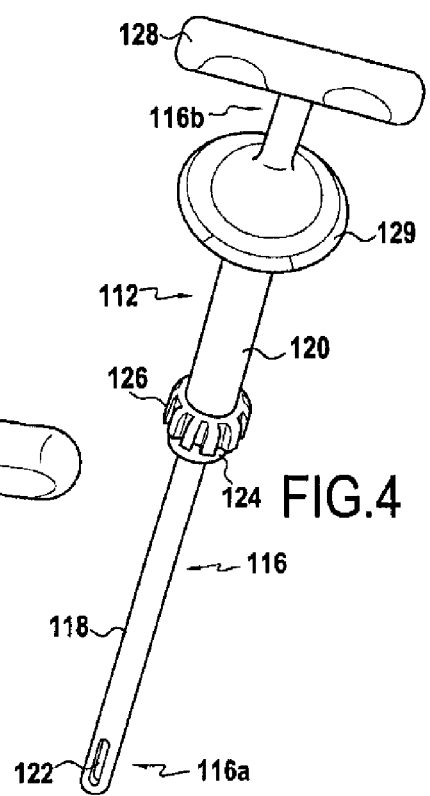
FIG. 4 is a perspective view of the longitudinal member of the surgical tool.
Figure 5:
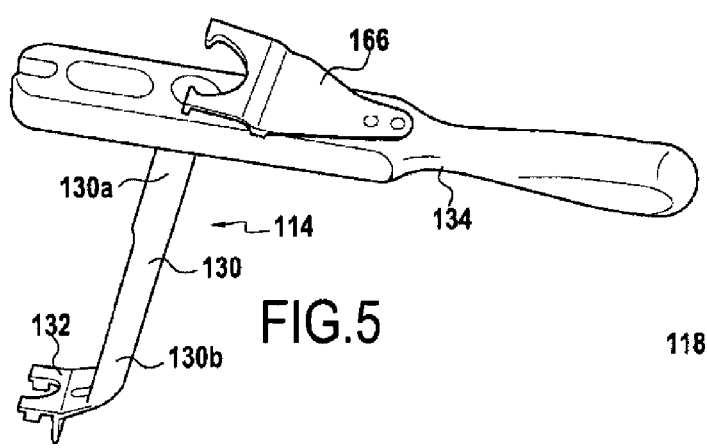
FIG. 5 is a perspective view of the guiding structure of the surgical tool.

Referring firstly to FIGS. 3 to 5, the general structure of the surgical tool for tensioning a flexible member will be described. The surgical tool 110 mainly comprises a longitudinal member 112 and a guiding structure 114.

According to the embodiment presently described, the longitudinal member 112 is a rod 116, such as a cylindrical rod, having a first distal end 116a and a second proximal end 116b. The rod 116 comprises a portion 118 of reduced diameter and a portion 120 of increased diameter. The distal end 116a of the longitudinal member, i.e. the distal end of the rod portion 118, is provided with a diametrical slot 122. The two ends of the slot 122 open into the outer surface of the cylindrical portion 118. The sizes of the cross section of the slot 122 are designed so that the two free extremities of a flexible member (not shown) can be inserted through the slot. At the connection between the portions 118 and 120 of the rod, the longitudinal member 116 is provided with a shoulder 124 and an annular portion 126.

At the proximal end 116b of the longitudinal member, i.e. at the proximal end of the portion 120, a handle 128 is mounted.

Preferably, a measurement system 129 may be provided in the portion 120 of the rod 116 below the handle 128 to measure the tension on the flexible member.

Referring now more particularly to FIGS. 3 and 5, the guiding structure 114 will be described.

In the embodiment shown in FIGS. 3 and 5, the guiding structure 114 comprises, for example, a tubular member 130, an engaging member 132, and a handling member 134 (or handling element). The handling member 134 is mounted at the proximal end 130a of the tubular member 130 and the engaging piece 132 is secured to the distal end 130b of the tubular member 130 and extends beyond the distal end 130b.

The inner diameter of the tubular member 130 is slightly greater than the external diameter of the rod 118 of the longitudinal member 116. As a result, the longitudinal member 116 can be freely rotated within the tubular member 130. Moreover, the proximal end 130a of the tubular member 130 is in abutment against the shoulder 124 provided at the proximal end of the rod 118. The rod 118 has a length which is longer than the one of the tubular member 130 so that, when the shoulder 124 is in abutment against the proximal end 130a of the tubular member 130, the distal end 116a of the longitudinal member 116 projects out of the tubular member with the slot 122 provided at the distal end of the rod 118 that is facing the engaging piece 132 (see FIG. 3).

The purpose of the engaging piece 132 is to maintain the surgical tool 110 in a fixed and predetermined position with respect to the vertebral device, the flexible member of which should be tensioned. The particular design of the engaging piece 132 is adapted to the configuration of the body of the vertebral device and to the location of the body from which the free extremities of the flexible member project out.

Figure 2:
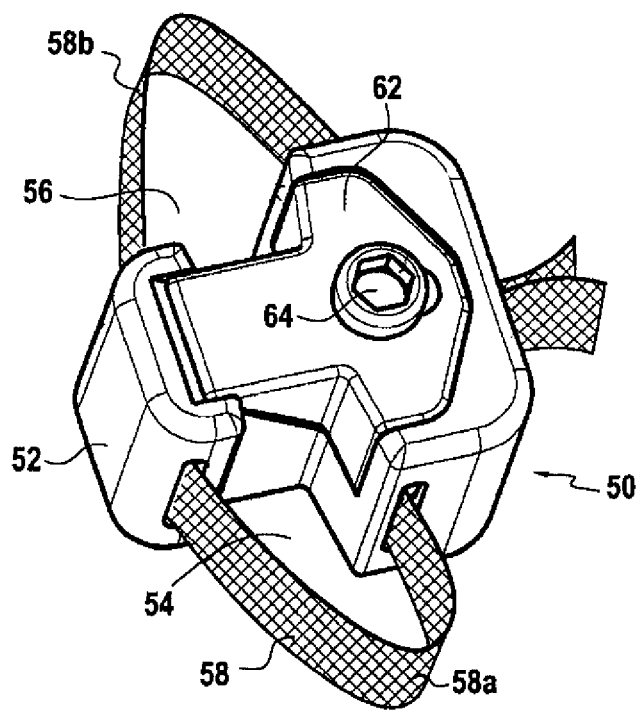
FIG. 2, described above, shows an example of an intervertebral implant with which the surgical tool can be used.
Figure 6:
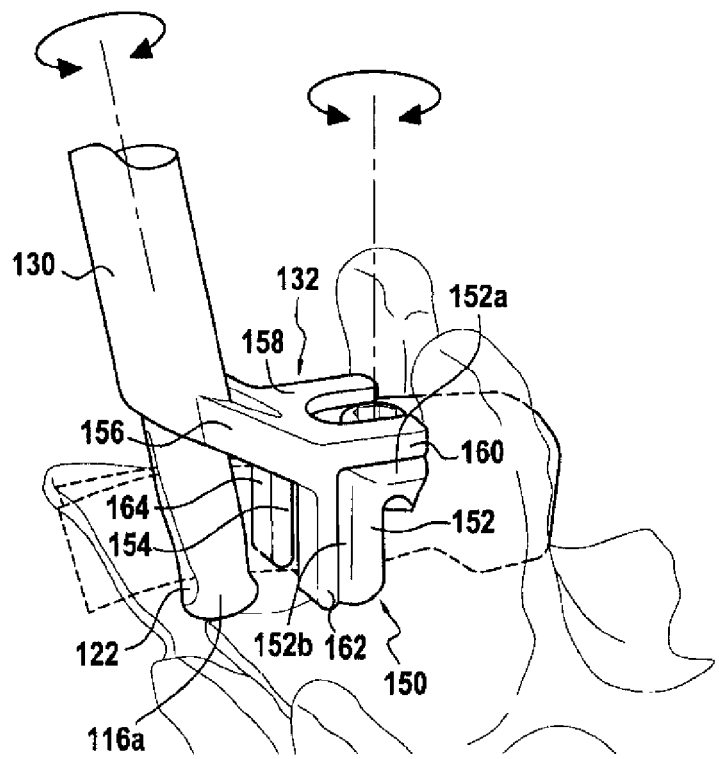
FIG. 6 is a perspective view showing the end of the surgical tool applied against the body of a vertebral device.

In the embodiment shown in FIG. 6, the vertebral device 150 is an intervertebral implant of the type shown in FIG. 2. In this figure is shown the body 152 of the intervertebral implant with its upper face 152a and its front face 152b, and the opening 154 provided in the front face 152b and from which the free ends of the flexible member project.

The engaging piece 132 comprises a connecting portion 156 secured to the distal end of the tubular member 130, two first arms 158 and 160 substantially perpendicular to the tubular member 130, and two second arms 162 and 164 substantially parallel to the tubular member 130. In use, the first arms 158 and 160 are applied against the upper face 152a of the implant body and the second arms 162 and 164 are applied against the front face 152b of the implant body on each side of the opening 154.

Figure 7A:
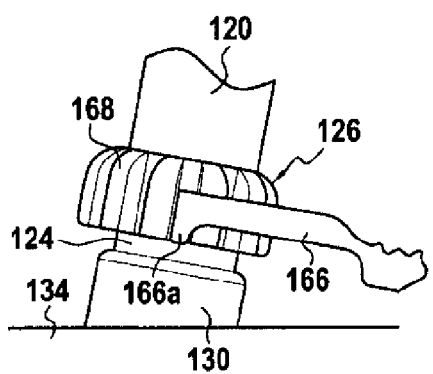
FIGS. 7A and 7B are perspective views showing the locking system of the surgical tool.

As already explained, the proximal end 130a of the tubular member 130 is provided with a handling element or handling member 134. The handling member 134 is equipped, close to the rod 118, with a first locking member consisting in a lever 166 pivotally mounted on the handling member 134. The second locking member consists of radial slots 168 provided on the outer surface of the annular portion 126. In a first locking position shown in FIG. 7A, the end 166a of the lever 166 is engaged in one of the radial slots 168.

Figure 7B:
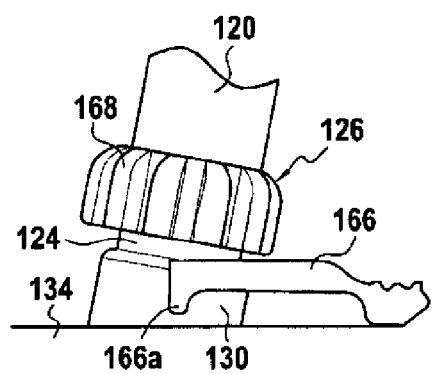

In a second unlocking position shown in FIG. 7B, the end 166a of the lever 166 is not engaged into one of the slots 168. In the first position of the lever 166, the longitudinal member 112 is secured in rotation with the guiding structure 114. In the second position of the lever 166, the longitudinal member 112 can be freely rotated within the guiding structure 114.

Now the use of the above described surgical tool will be explained when applied to the tensioning of the flexible member of an intervertebral implant of the type shown in FIG. 2. However, the use of the surgical tool for tensioning the flexible member of other vertebral devices is similar.

In a first step, the surgeon inserts the body of the intervertebral implant between the spinal processes of two adjacent vertebrae. Moreover, the surgeon places two loops of the flexible member around the spinal processes and makes the two end portions of the flexible member project out of the implant body through the opening 154.

In a second step, the surgeon inserts the two ends of the flexible member through the slot 122 of the longitudinal member 112 so that these extremities project out of the slot. In other embodiments, the surgeon may only insert one free end portion of a flexible member.

Then, the surgeon properly places the engaging piece 132 of the tool against the body of the intervertebral implant, as explained previously.

The surgeon maintains the engaging piece 132 against the implant body by means of the handling member 134 of the guiding structure 114.

Subsequently, the surgeon rotates the longitudinal member 112 by acting on the handle 128. The flexible member is rolled around the distal end of the rod 118 and consequently tension is applied to the flexible member.

When the measurement system indicates that a proper tension is being applied to the flexible member, the surgeon stops rotating the longitudinal member 112.

In the following step, the surgeon moves the locking lever 166 so that it is inserted into the corresponding slot 168 of the annular portion 126. The intensity of the tension applied to the flexible member is maintained.

Then, the surgeon can rotate the screw 64 of the intervertebral implant 150 to pinch the two portions of the flexible member between the body 152 of the intervertebral implant and the movable part 62 thereof.

As a result, the intervertebral implant 150 is secured to the two spinal processes with a correct tension and the surgeon can remove the surgical tool 110 from the patient's spine.

Figure 1:
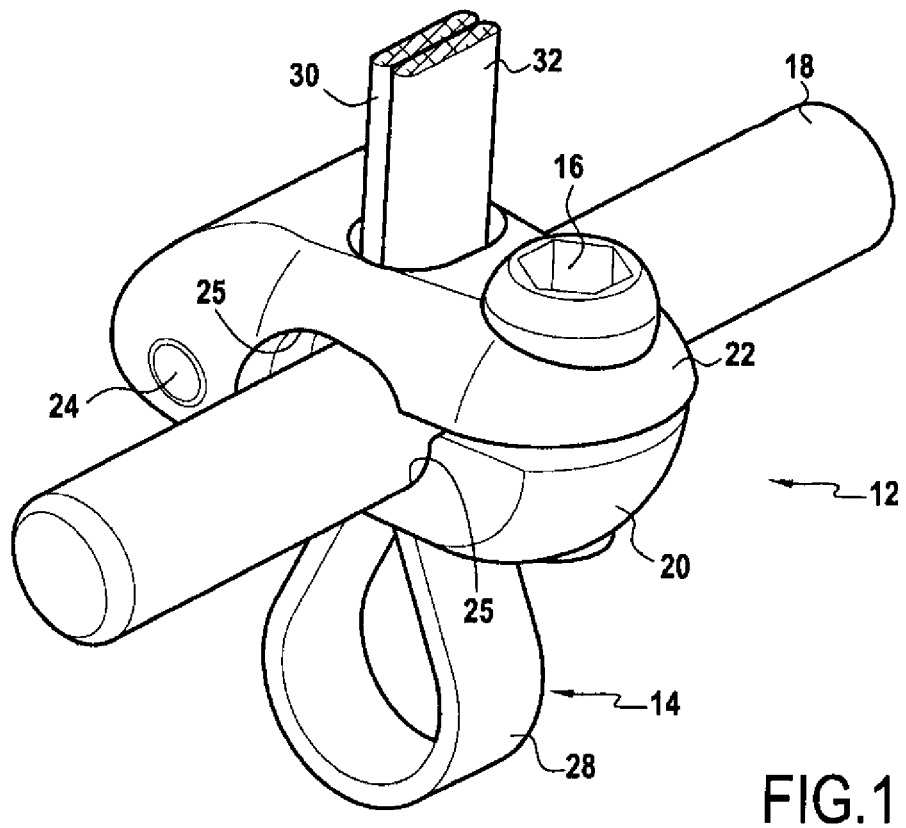
FIG. 1, described above, shows one example of a device for fastening a rod to a vertebra by means of a flexible member with which the surgical tool can be used.
Figure 8:
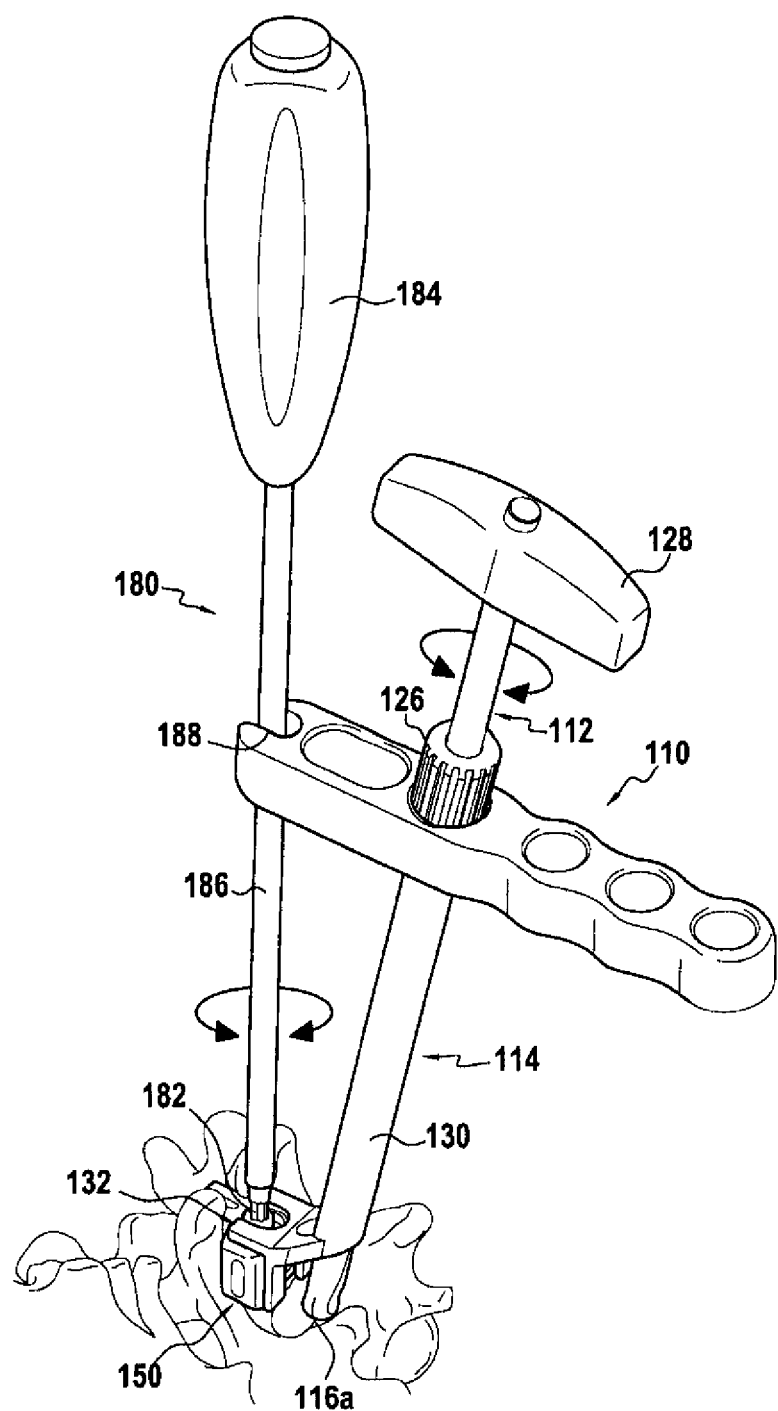
FIG. 8 is a perspective view showing a variant of the surgical tool.

As shown in FIG. 1 or 2, the vertebral device comprises a locking screw to pinch the flexible member in the body of the vertebral implant. The embodiment of the surgical tool shown in FIG. 8 facilitates the action of the surgeon to screw the locking screw of the vertebral device. The surgical device further comprises a screwing tool 180 having an end 182 adapted to the particular type of the screw of the vertebral device and a handle 184. The current part 186 of the screwing tool is engaged in a hole or slot 188 provided in the handle 134 of the guiding structure 114.

The invention claimed is:

1. A surgical tool for tensioning a flexible member of a vertebral device having a body, said flexible member having at least one end portion to which tension is applied, said tool comprising:
   a longitudinal member having a longitudinal axis, a first end provided with an element for securing in rotation the at least one end portion of said flexible member with said first end of the longitudinal member, and a second end provided with a handling element; and
   a guiding structure comprising a first end adapted to be applied against said body of the vertebral device, and at least one guiding member for guiding in rotation with respect to said guiding member said longitudinal member about said longitudinal axis, said guiding structure maintaining the longitudinal axis of the longitudinal member with respect to said body, whereby the rotation of said longitudinal member with said handling element and with respect to the guiding member produces the tensioning of said flexible member in a direction perpendicular to the longitudinal axis;
   wherein the first end of said longitudinal member is designed for rolling said at least one end portion of the flexible member when said longitudinal member is rotated.

2. The surgical tool according to claim 1, wherein said element for securing at least one end portion of the flexible member comprises a slot designed for receiving said at least one end portion of the flexible member.

3. The surgical tool according to claim 1, wherein said longitudinal member is a rod having first and second ends, and said guiding member is a tubular member having first and second ends and adapted to receive said rod in rotation.

4. The surgical tool according to claim 3, wherein said first end of said tubular member is provided with an engaging piece to be applied against said body of the vertebral device for securing in rotation said tubular member with respect to said body.

5. The surgical tool according to claim 4, wherein said second end of the tubular member is provided with a second handling element.

6. The surgical tool according to claim 5, further comprising a screwing tool for cooperating with a screw of said vertebral device and wherein said second handling element comprises a portion for guiding in rotation said screwing tool.

7. The surgical tool according to claim 3, wherein said rod comprises first rotation locking elements and said tubular member comprises second rotation locking elements for controllably cooperating with said first rotation locking elements, whereby said rod can be controllably secured in rotation with relative to said tubular element.

8. The surgical tool according to claim 7, further comprising a measurement system mounted at said first end of the rod to measure the tension of the flexible member.

9. The surgical tool according to claim 1, further comprising a locking member for securing in rotation said longitudinal member and relative to said guiding structure.

10. The surgical tool according to claim 1, further comprising a screwing tool for cooperating with a screw of the vertebral device.

11. A surgical tool for tensioning a flexible member of a vertebral device having a body, said flexible member having at least one end portion to which tension is applied, said tool comprising:
- a longitudinal member having a longitudinal axis, a first end provided with an element for securing in rotation the at least one end portion of said flexible member with said first end of the longitudinal member, and a second end provided with a handling element; and
- a guiding structure comprising a first end adapted to be applied against said body of the vertebral device, and at least one guiding member for guiding in rotation with respect to said guiding member said longitudinal member about said longitudinal axis, said guiding structure maintaining the longitudinal axis of the longitudinal member with respect to said body, whereby the rotation of said longitudinal member with said handling element and with respect to the guiding member produces the tensioning of said flexible member;
- wherein the first end of said longitudinal member is designed for rolling said at least one end portion of the flexible member when said longitudinal member is rotated.

* * * * *